US00PP08254P

United States Patent [19]

Rosenbaum

[11] Patent Number: Plant 8,254

[45] Date of Patent: Jun. 15, 1993

[54] SEEDLESS FIG TREE 'JANICE'

[76] Inventor: Percy W. Rosenbaum, 5587 Tyler Pl., Fremont, Calif. 94538

[21] Appl. No.: 767,236

[22] Filed: Sep. 27, 1991

[51] Int. Cl.[5] ..... A01H 5/00
[52] U.S. Cl. ..... Plt./33.1
[58] Field of Search ..... Plt. 33, 51, 68, 33.1, Plt./88.9

[56] References Cited

PUBLICATIONS

Childers, Norman F., "The Fig" *Modern Fruit Science* (4th Ed.) 1969 pp. 489–497.

Storey, W. B., "Figs" *Advances in Fruit Breeding* (Editors, Janick, J., et al.) 1975, Purdue University Press, West Lafayette, Ind., pp. 568–589.

*Primary Examiner*—James R. Feyrer
*Attorney, Agent, or Firm*—Robert Charles Hill

[57] ABSTRACT

A new and distinct variety of the common fig tree, *Ficus carica,* characterized by producing large, sweet, light green fruits that do not contain brittle endocarps.

1 Drawing Sheet

BACKGROUND OF THE NEW TREE

The present invention comprises a new and distinct variety of fig tree, *Ficus carica.* This new and distinct variety was found by the inventor in a cultivated area in San Luis Rey, Calif., which tree came from a sport branch or limb from a regular Kadota fig tree in Santa Ana, Calif. The inventor obtained hardwood cuttings from this tree in San Luis Rey and propagated them asexually in Fremont, Calif.

The most significant feature of this new and distinct variety is that the fruits of this tree have no brittle endocarps, thereby differing from the usual seeded fruits of the commercial fig varieties. This new and distinct variety has been found to retain its distinctive characteristic (minus brittle endocarps) through successive propagations. The fruits of this new and distinct variety have been named "Janice" Kadota figs by the inventor.

Another clear characteristic which is not inherent in other fig varieties is the productivity of this fig tree without endocarps. The tree bears fruit heavily each year. Crops are borned later in the season then for most commercial fig varieties. A first crop matures about August first, a second, about September first, a third the heaviest, about October first, and later crops mature until the first frost. In addition, the ostiole is smaller because it is very tight while the fruit itself is larger than its species of origin. In fact, the fruit of this new and distinct variety measure about 2¼ inches in diameter as compared to a diameter of slightly under 2" in diameter for fruit from the source.

DESCRIPTION OF THE DRAWINGS

FIG. 1 is a color photograph showing various aspects of the new fig tree.

The top left shows a yearling branch.

The top middle and right show the end of a branch with the front and back side of a leaf.

The lower middle and right show a whole flat leaf.

The middle and lower left contain 3 pictures of the fruit, and the left middle shows the fruit cut in half to indicate a lack of brittle endocarps.

DESCRIPTION OF THE NEW TREE

The following description was developed from fruit and plant material taken from young trees of the new variety growing at Fremont, Calif. Color references are from "Dictionary of Color" by Maerz and Paul, first edition published in 1930.

Fruit

*Form.*—The fruit body is spherical with usually a short neck present. A moderate percentage of fruit have no neck present at all.

Size.—Medium to large in size. Fruit width ranges from 50 to 58 mm in diameter and from 48 to 60 mm in length not including the peduncle.

*Neck.*—Most often the neck is short and tapered, but occasionally almost no neck is present at all. Neck coloration is in the same color ranges as the general skin color.

*Peduncle.*—Medium in length and slightly curved. Length ranges from 11 to 17 mm. The peduncle is moderately thick from 4.0 to 5.0 mm. Peduncle color ranges from a medium green (19-L-7) to a lighter green-yellow (18-K-3). Peduncle bracts are low, relatively small and slightly appressed to the fruit.

*Skin.*—The skin adheres to the meat over the ostiole end of the fruit but can be readily peeled back from the stem end. The skin is glossy and the external skin color at full maturity is a yellow-green (18-L-2 Citronella Green) to a more green-yellow (18-K-6) on less mature fruit. Skin texture is firm and slightly rubbery. Moderate longitudinal skin checking is present on the ripest fruit. A relatively delicate grey bloom is present over the skin surface. Short and sparse epidermal hairs are present throughout the skin surface. Numerous white flecks are also present over the skin surface, from nearly globose to oval in form, with the most elongated flecks present near the ostiole end of the fruit.

*Fig interior.*—The meat of the Janice fig lying between the skin and the pulp is most frequently white (1-A-1). The pulp which makes up the remainder of the interior of the fig fruit (the inner part of the meat and the floral parts) is usually amber-yellow in color (11-K-4 Glint O'Gold) when fully mature. The pulp fills the entire center of the fig and is relatively fine textured. The interior surfaces are lined with long styled pistillate flowers. A few scattered infertile seeds are present in the fruit of the Janice fig. These seeds are greatly reduced in number in comparison with the typical Kadota variety. The seeds are very small and tan in color (11-K-6 Rattan).

*Flavor.*—The Janice fig is very sweet and mild flavored with good quality.

*Use.*—The principal use of this fig is for fresh market.

LEAF AND TREE DESCRIPTION

Leaves:

*Form.*—Base calcarate, most frequently five lobed although some variation is present. The lobes are latate in form.

Leaf

*Size.*—Leaf measurements are taken from large leaves on relatively young trees. Leaf size is large. Leaf length is variable from 20.9 to 25.1 cm from the leaf apex to the petiolar junction. Leaf width ranges from 23.2. to 24.6. cm.

*Sinuses.*—Upper sinuses are relatively deep and "U" shaped. The petiolar sinus is relatively shallow and "V" shaped.

*Margins.*—Much variability exists, but the margins can generally be characterized as irregularly crenate.

*Color.*—Upper leaf surface a deep green (24-J-8). The main veins are a very light green (18-I-4). Lower leaf surfaces are a lighter grey-green (21-H-6). Lower vein color is also a pale green (17-I-3). Leaf surface rather dull with low light refraction.

*Petiole.*—Medium in length from 6.9 to 8.4 cm. Petiole color variable from a light olive green (14-K-1) to a lighter green-yellow (20-I-1).

Trunk: Relatively smooth in texture with average diameter. Bark color a medium grey (6-A-7).

Branches: Mature branches smooth with average diameter. Branch color varies from a deep green-brown (16-C-7) to medium brown (15-L-12 raw Umber). Immature current season's growth a medium green (22-L-8). Small light colored lenticels are often apparent on the young shoots.

Buds: The terminal buds are conical in shape with a relatively acute lip. Terminal bud color is a light green (20-L-6). Bud scales often become brownish as they separate and slough off of the expanding meristem. Fruit buds are more rounded in shape at their apex and are approximately the same color as the terminal bud.

Tree form: Existing trees of the Janice variety are relatively young at this date but appear so far to be upright to upright-spreading in their growth habit.

Summary: The above described Janice fig can be characterized as a high quality, green skinned fig of the common type, suited for use as a fresh market fig. The fig is similar to the Kadota fig variety from which it originates, in most characteristics of the tree, leaves and fruit. The single most distinctive difference between the Janice and the Kadota is the substantial reduction in the number of seeds produced inside the Janice fig in comparison with the Kadota.

I claim:

1. A new and distinctive variety of fig tree substantially as described and characterized particularly by a lack of brittle endocarps within the fruit.

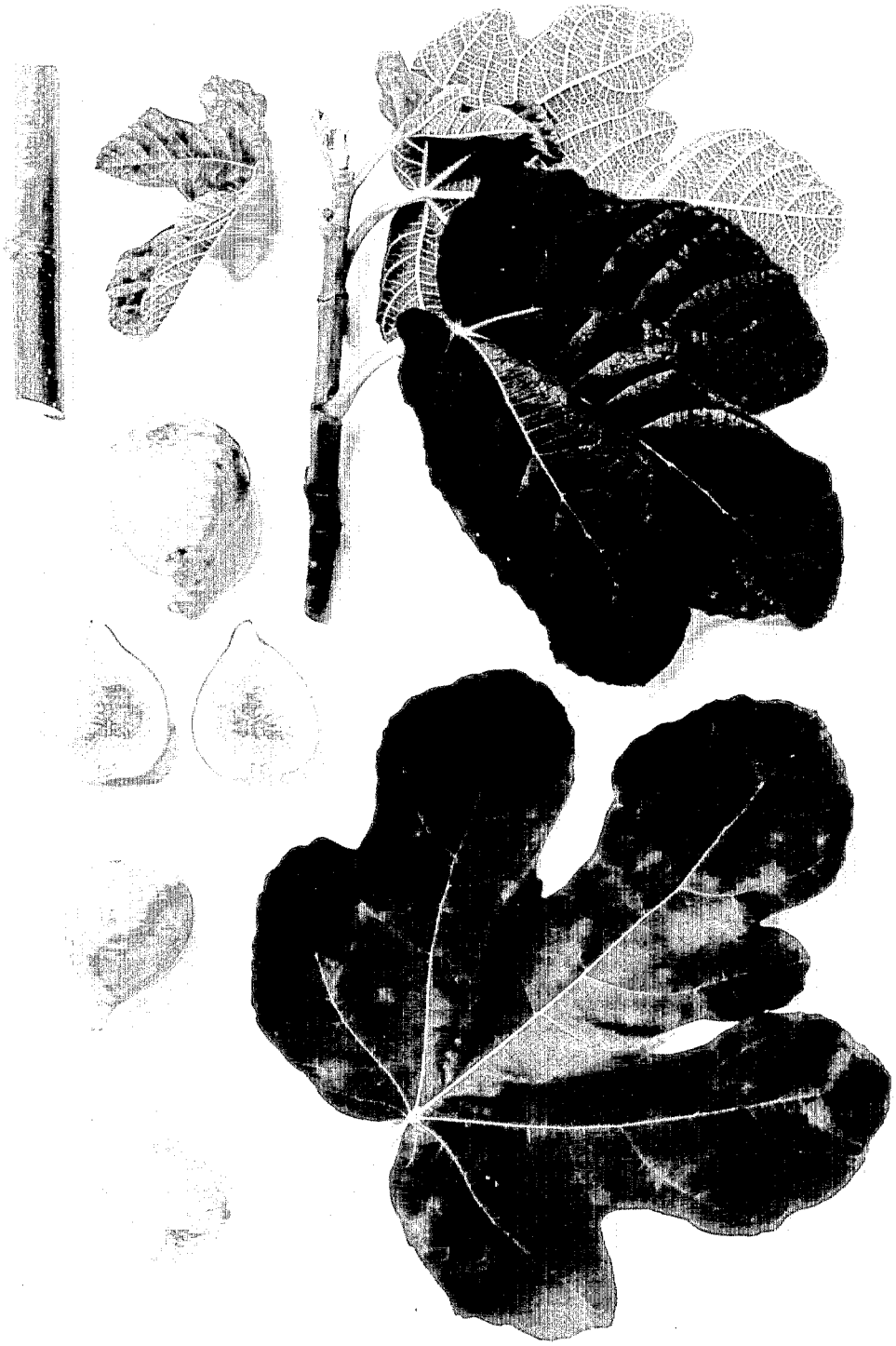

* * * * *